United States Patent [19]

Christensen et al.

[11] Patent Number: 5,766,243

[45] Date of Patent: Jun. 16, 1998

[54] ABRASIVE POLISHED CANALICULAR IMPLANT

[75] Inventors: James Marlow Christensen, Glendora; Willis Joseph Bruns, Redlands, both of Calif.

[73] Assignee: Oasis Medical, Inc., Glendora, Calif.

[21] Appl. No.: 690,052

[22] Filed: Jul. 31, 1996

Related U.S. Application Data

[63] Continuation of Ser. No. 517,338, Aug. 21, 1995, abandoned.

[51] Int. Cl.$^6$ ............................................. A61F 2/14
[52] U.S. Cl. ........................ 623/4; 623/900; 604/294; 451/32
[58] Field of Search ........................ 623/901, 4, 11; 604/8, 9, 11, 15, 285, 294, 295; 264/293, 162; 451/32, 326

[56] References Cited

U.S. PATENT DOCUMENTS

| | | | |
|---|---|---|---|
| 2,807,020 | 9/1957 | Schell | 451/32 |
| 3,949,750 | 4/1976 | Freeman | 604/294 |
| 4,898,186 | 2/1990 | Ikada et al. | 623/16 |
| 4,911,687 | 3/1990 | Stewart et al. | 604/11 |
| 4,959,048 | 9/1990 | Seder et al. | 604/9 |
| 5,049,142 | 9/1991 | Herrick et al. | 604/294 |
| 5,133,159 | 7/1992 | Nelson | 51/313 |
| 5,171,220 | 12/1992 | Herrick | 623/11 |
| 5,423,777 | 6/1995 | Tajiri et al. | 604/294 |
| 5,447,465 | 9/1995 | Samsel et al. | 451/32 |

FOREIGN PATENT DOCUMENTS

| | | | |
|---|---|---|---|
| 0262893 | 4/1988 | European Pat. Off. | 604/294 |

*Primary Examiner*—John G. Weiss
*Assistant Examiner*—Bruce E. Snow
*Attorney, Agent, or Firm*—Loeb & Loeb LLP; Michael J. Ram

[57] ABSTRACT

A canalicular implant for insertion through the punctum of the eye and the method of manufacture. The implant is fabricated by cutting suture-like material, such as catgut, of the appropriate diameter to the desired length. The ends of the implant are rounded and polished after cutting by abrasive polishing to remove any sharp edges and burrs formed by the cutting process. This produces an implant with various degrees of rounding at the ends depending on the duration and type of abrasive polishing used. The method of abrasive polishing may comprise tumble polishing, vibratory polishing, or other methods of agitation utilizing dry or wet media comprised of beads, forms, abrasive powders, or other similar substances or combinations of these media.

5 Claims, 1 Drawing Sheet

DIRECTION OF CUT

ABRASIVE POLISHED CANALICULAR IMPLANT

This is a continuation, of application Ser. No. 08/517, 338, filed Aug. 21, 1995, now abandoned.

FIELD OF INVENTION

This invention relates to an implant and a method of manufacturing the implant for treatment of the human eye having a deficiency of tears. More particularly, this invention relates to an implant for insertion into the canaliculus of the eye wherein the implant has rounded edges produced by abrasive polishing as the final step in the implant fabrication.

BACKGROUND OF INVENTION

It is known in the art that certain eye problems are related to the volume of tears on the surface of the eyes. Certain of these problems include dry eyes, corneal ulcers, conjunctivitis, blepharitis, contact lens problems, and many other external eye diseases. The preferred method of invasively treating a deficiency of tears is to block the flow of tears through the canaliculus with either an absorbable or non-absorbable implant.

Various styles of implants have been used to block the flow of tears from the eye in people suffering from dry eye syndrome. These implants have generally been of two types: non-absorbable implants primarily molded from silicone elastomer into several configurations; and, absorbable implants which are fabricated by cutting strands of catgut suture of appropriate diameter to the desired length.

The non-absorbable implants are exemplified by U.S. Pat. Nos. 3,949,750 and 5,334,137 to Freeman, U.S. Pat. No. 4,915,684 to MacKeen et al, and U.S. Pat. No. 4,959,048 to Seder et al, all of which show configurations of implants designed to block the punctual opening leading to the canaliculus. These implants have a portion of the implant externalized on the eyelid with the remainder of the implant positioned across the punctum and into the canaliculus. The non-absorbable implants are also exemplified by U.S. Pat. Nos. 5,049,142 and 5,053,030 and 5,171,270 to Herrick, all of which show configurations of implants designed to block the canaliculus. These implants are totally contained within the canaliculus. All commercially available non-absorbable implants corresponding to these patents are molded from silicone elastomer and have soft formed ends for insertion through the punctual opening.

Absorbable implants are exemplified by U.S. Pat. No. 5,049,142 to Herrick. This patent shows an illustration of a canalicular implant with squared off ends which is described as a piece of absorbable material, such as 3-0 catgut suture, which is 5 mm long. The implant is fabricated by cutting the appropriate size of catgut suture to the desired length. This style of absorbable canalicular implant as described and shown in FIG. 2 of U.S. Pat. No. 5,049,142 is easy to fabricate and low in cost. In the same patent are shown several drawings (FIG. 3–11) of non-absorbable canalicular implants which would typically be molded from silicone elastomer or other such material. Each of these drawings show a non-absorbable implant with tapered ends. The patent describes these configurations as further facilitating the insertion of the non-absorbable implant, while Herrick claims a tapered end on an absorbable material. None of the prior art references disclose a product or method to manufacture an absorbable implant with rounded ends. All commercially available absorbable canalicular implants sold have squared off ends. The resultant cut ends of the implant are sharp and usually deformed in the direction of cutting to create a burr which snags the tissues of the punctum and canaliculus during insertion and can produce discomfort after insertion until the catgut begins to soften and resorb.

What is needed is a low cost method of removing the sharp edges and any burrs formed after cutting the catgut suture to length. This would provide an absorbable canalicular implant that would be easy to insert and comfortable for the patient.

SUMMARY OF INVENTION

It is therefore a general object of the present invention to provide an improved canalicular implant for blocking tear flow from the human eye and to provide a method of fabricating the improved canalicular implant.

It is another object of the present invention to provide an improved canalicular implant wherein the ends of the implant have been rounded to remove any sharp edges or burrs caused by fabrication.

It is yet another object of the present invention to provide a method wherein the improved canalicular implant is rounded and polished by abrasive polishing after it has been fabricated.

It is still another object of the present invention to provide an absorbable canalicular implant cut from suture-like material which has rounded ends formed by abrasive polishing.

It is a further object of the present invention to provide a novel method for rounding the ends of an absorbable canalicular implant by abrasive polishing after it has been cut from suture-like material in order to remove sharp edges and burrs.

BRIEF DESCRIPTION OF DRAWINGS

The foregoing and other advantages of the present invention will be apparent from the following description of the preferred embodiment of the invention when considered with the accompanying drawings which include the following Figures.

DETAILED DESCRIPTION OF THE INVENTION

Figure 1:
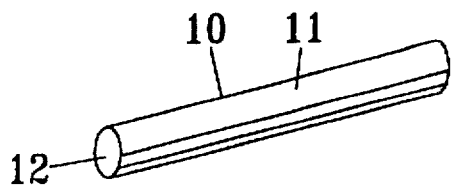
FIG. 1 is a perspective view of a commercially available absorbable canalicular implant having a cylindrical cross-section.

As illustrated in FIG. 1, a commercially available absorbable canalicular implant 10 includes an elongated central portion 11 of cylindrical geometry with squared-off end portions 12 on either side of the central portion 11. The commercially available implant is formed by cutting catgut suture of the appropriate diameter to the desired length. The diameter of the central portion 11 typically ranges from 0.2 mm to 0.7 mm. The length of the central portion 11 typically ranges from 1.6 mm to 2.5 mm.

Figure 2:
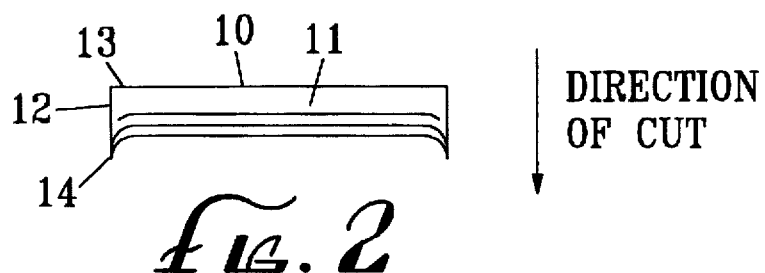
FIG. 2 is a side view of a commercially available absorbable canalicular implant showing the sharp edges and burrs that are formed when the implant is cut to length from suture-like material.

FIG. 2 shows a side view of the commercially available absorbable canalicular implant 10. The sharp edges 13 and the burr 14 are formed at the end portions 12 when the implant is cut from the catgut suture material. The direction of cut is shown in FIG. 2. Burrs 14 are formed during the cutting process as the soft catgut material is deformed beyond the edge of the suture by the cutting blade. These burrs 14 and sharp edges 13 cause the implant to snag on the punctual and canalicular tissues as the implant is being inserted. Similar sharp edges 13 and burrs 14 would be formed to some degree when any suture-like material is cut.

Figure 3:
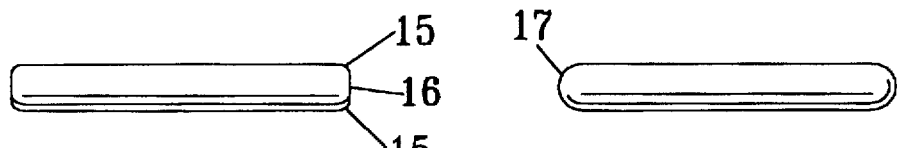
FIG. 3 is a side view showing the rounded edges obtained after mild abrasive polishing of the absorbable canalicular implant shown in FIG. 2.
Figure 4:
FIG. 4 is a side view showing the rounded edges obtained after moderate abrasive polishing of the absorbable canalicular implant shown in FIG. 2.
Figure 5:
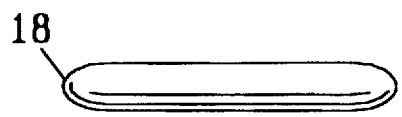
FIG. 5 is a side view showing the rounded edges obtained after prolonged abrasive polishing of the absorbable canalicular implant shown in FIG. 2.

To remove these sharp edges 13 and burrs 14, the cut implants are abrasively polished. Mild abrasive polishing produced an implant having rounded edges 15 and a flat end 16 as shown in FIG. 3. Moderate abrasive rounded edges 15 and a flat end 16 as shown in FIG. 3. Moderate abrasive polishing achieved by increasing the duration of polishing or changing to a more aggressive media will produce an implant having a more fully rounded end 17 as shown in FIG. 4. Prolonged abrasive polishing will eventually begin to taper the ends of the implant to produce a tapered and rounded end 18 as shown in FIG. 5.

Abrasive polishing can be achieved through tumble polishing in a rotating barrel, vibratory polishing in a vibrating bowl, or other similar methods of agitation. In each of these methods a large quantity of implants cut to the approximate desired length are placed in a container along with a selected abrasive media and then tumbled, vibrated, or agitated for a period of time, usually several days. The time period and media are selected to achieve the degree of rounding or tapering desired for the implants. Usually a different time period will be used for each diameter of implant to be rounded. At the end of the time period the implants are separated from the media then washed and packaged.

Abrasive polishing can be performed in either a wet or dry media. The media may be wetted with any suitable fluid, such as water, detergent, alcohol, oil or thickener, which does not dissolve or soften the material of the implant and the abrasive medias involved. Different degrees of abrasive cutting and polishing are achieved by using a wet or dry media. For catgut suture, which is softened by the absorption of water or alcohols, the abrasive polishing media is preferably dry. The use of a wet media would cause the catgut suture, which is formed by twisting a thin sheet of intestinal tissue into a suture shape, to unravel and flare out at the ends and soften.

There are a multitude of media and combinations of media that can be used for abrasive polishing. Glass or ceramic beads or forms can be used to obtain minimal edge rounding. The typical size range of these abrasives to polish catgut implants is from about 0.5 mm to about 3 mm diameter. Various water soluble crystalline substances, such as table salt or sugar, can be used to achieve mild abrasive polishing. The advantages of salt and sugar is the ability to dissolve the media in order to separate the abrasive media from the implants after tumbling. For more aggressive abrasive polishing, abrasive powders such as alumina, silica, pumice, etc. can be added to a media of glass or ceramic beads or similar media. The beads act as carriers for the abrasive powder. The choice of media size is important as different size media are in greater or lesser contact with the implants depending on the size of the media and the open spacing between the media. This influences the degree of rounding that can be achieved at the ends of the implant. Frequently a mixture of media sizes are used to obtain optimum abrasive action.

The operating parameters of the equipment and the container which holds the cut implants and the media have a significant affect on the abrasive polishing process. The containers are filled to the appropriate level for the method of abrasive polishing chosen so that proper media movement can be achieved inside the container. The operating parameters of the equipment are adjusted consistent with the container and media to be used to obtain proper tumbling, vibratory, or agitation action. For example, in tumble polishing, the barrel is sized so that a layer of media can slide down over the other media in the barrel during rotation rather than being flung in the air to the bottom of the barrel. In vibratory polishing the frequency of vibration is adjusted so that it is in resonance with the mass of the media in the bowl. The materials of construction of the barrel can also have an effect on the abrasive polishing process. Plastic containers can develop a static charge which could cause the implants to accumulate in a low action portion of the container. Glass or metal containers appear not to have this problem.

EXAMPLE 1

A 3-inch diameter by 4-inch long glass tumbling jar was half filled with table salt and 1000 pieces of 3-0 catgut suture cut to 2.0 mm long were added to the jar. The jar was tumbled at a speed of approximately 80 RPM for 4 days. At the end of this period the catgut pieces had an appearance as in FIG. 3 with the edges rounded to a radius equal to ⅛ the diameter of the catgut piece, the remainder of the ends being flat. The entire surface of the catgut implant was also polished smooth.

EXAMPLE 2

Into a 3-inch diameter by 4-inch long glass tumbling jar one-third full of of 1.6 mm to 2.5 mm zirconium beads was added 30-grams of 50-micron glass beads and 1000 pieces of 3-0 catgut suture cut in 2.0 mm lengths. The jar was tumbled at a speed of approximately 80 RPM for 5 days. At the end of this period the edges of the catgut pieces were rounded with little or no flat ends (similiar to FIG. 4). The entire surface of the catgut implant was polished smooth.

While the examples are directed to absorbable material, namely catgut, the techniques described herein are also applicable to other absorbable or water swellable materials such as polyglycolic acid, hydroxyethylmethacrylate (HEMA) and non-absorbable materials such as nylon, propylene, etc.

In describing the invention, reference has been made to preferred embodiments. Those skilled in the art, and familiar with the disclosure of the subject invention, may recognize additions, deletions, modifications, substitutions, and/or other changes which will fall within the purview of the invention as designed in the following claims.

What it claimed is:

1. A method of forming rounded end sections on an implant used for blocking the flow of tear fluid from the surface of the eye through the canaliculus comprising severing a continuous length of a material absorbable in the human body into predetermined lengths to form cylindrical implants;

placing the cylindrical implants in a container partially filled with a particulate abrasive media;

causing the cylindrical implants to be continuously impacted with the particulate media so as to abrade all surfaces of the implant and eliminate any sharp edges on the implant, the continuous impaction creating polished surfaces and separating the cylindrical implants from the abrasive media.

2. The method according to claim 1 wherein the implant is cut from a suture-like material.

3. The method according to claim 2 wherein the suture-like material is catgut suture.

4. The method according to claim 1 wherein the continuous impacting is accomplished by tumbling the implants and media together.

5. The method according to claim 1 wherein the continuous impacting is accomplished by placing the implants and media in intimate contact on a vibrating surface.

* * * * *